(12) United States Patent
Laerdal et al.

(10) Patent No.: US 8,696,648 B2
(45) Date of Patent: Apr. 15, 2014

(54) NASAL ASPIRATOR

(75) Inventors: Tore Laerdal, Stavanger (NO); Jens Petter Ianke, Sola (NO); Kjell Ove Korneliussen, Sandnes (NO)

(73) Assignee: Laerdal Medical AS, Stavanger (NO)

( * ) Notice: Subject to any disclaimer, the term of this patent is extended or adjusted under 35 U.S.C. 154(b) by 113 days.

(21) Appl. No.: 13/262,021

(22) PCT Filed: Apr. 28, 2010

(86) PCT No.: PCT/EP2010/055705
§ 371 (c)(1),
(2), (4) Date: Sep. 29, 2011

(87) PCT Pub. No.: WO2010/125095
PCT Pub. Date: Nov. 4, 2010

(65) Prior Publication Data
US 2012/0029486 A1   Feb. 2, 2012

(30) Foreign Application Priority Data
May 1, 2009 (NO) .................................. 20091729

(51) Int. Cl.
*A61M 1/00* (2006.01)
(52) U.S. Cl.
USPC ........................................ 604/540; 604/132
(58) Field of Classification Search
CPC ....... A61M 1/00; A61M 5/178; A61M 35/00; A61M 5/32; A61N 1/30
USPC ..................... 604/540, 19, 37, 54, 296, 298, 604/131–133, 197, 275
See application file for complete search history.

(56) References Cited

U.S. PATENT DOCUMENTS

| 2,234,884 | A | * | 3/1941 | Teel | 239/327 |
| 2,890,699 | A | | 6/1959 | Miller | |
| 4,487,336 | A | * | 12/1984 | Sneider | 222/107 |
| 5,114,415 | A | | 5/1992 | Shedlock | |
| 6,290,667 | B1 | * | 9/2001 | Cook | 604/19 |
| 2007/0270736 | A1 | | 11/2007 | Giarrocco-Brettner | |

FOREIGN PATENT DOCUMENTS

| EP | 0451062 A1 | 10/1991 |
| FR | 2920313 A1 | 3/2009 |

OTHER PUBLICATIONS

Lakkis, Angeliki, "International Search Report", for PCT/EP2010/055705, as mailed Jan. 5, 2011, 3 pages.

* cited by examiner

*Primary Examiner* — Tatyana Zalukaeva
*Assistant Examiner* — Benedict L Hanrahan
(74) *Attorney, Agent, or Firm* — Winstead PC

(57) ABSTRACT

A nasal aspirator comprising a resilient bulb and a stem for suction of liquids by vacuum created by compressing the bulb and thereafter gradually releasing the compression of the bulb, where the stem is removable connected to the bulb part, wherein the bulb part comprises a neck portion adopted to interact with a cap portion of the stem part to create a substantially airtight connection there between.

3 Claims, 2 Drawing Sheets

NASAL ASPIRATOR

TECHNICAL FIELD

The present invention relates to an improved bulb suction device. More specifically the present invention relates to a bulb suction device for medical purposes such as clearing the upper airways of a small child or a newborn for liquids.

BACKGROUND ART

Medical bulb suction devices, or aspirators, are well known and are used e.g. for clearing the airway of a newborn for liquids so that the baby can breath. This kind of suction devices may also be used to remove liquids such as mucus from the upper airway of children, or to remove meconium.

The known aspirators fall into two main categories:
1. Manually operated suction devices
   a. Bulb suction devices, where vacuum is generated by squeezing a self-expanding small bulb
   b. Mouth suction devices (so called De Lee suction), where the vacuum is generated by the rescuer's mouth
   c. Other hand operated suction devices, where vacuum typically is generated by the operator pulling a handle and using a pistol type grip on the device
   d. Foot operated suction devices, where vacuum is generated by the operator stepping on a foot pump
2. Self powered suction devices
   a. Battery or mains driven suction devices,
   b. Wall suction devices, that are connected to a wall mounted source of vacuum The recommended and most commonly used suction devices outside a hospital or a health centre environment are manually operated suction devices, and primarily bulb suction devices. Bulb suction devices are normally the only recommended aspirators in developing countries as they are simple to operate and relatively inexpensive.

The nasal aspiration devices of the bulb suction type comprises a bulb made of a compressible, elastic material, connected to a hollow stem that is fluidly connected to the inside of the bulb and is designed to be inserted into a nostril. Preferably, at least the outer tip to be inserted into a nose is made of a pliable material to avoid damaging the mucosal membrane inside the nose. The stem may also be conical or have a stepwise widening of the outer diameter, or be provided with a stopper, to avoid that the stem is inserted to deep into the nostril.

In use the user of the device compresses the bulb, inserts the stem into a nostril or mouth of the baby/child and releases the compression of the bulb gradually to withdraw mucus and secretions from the nostril or mouth. The sucking force can be controlled by the user by controlling the compressive forces at the bulb.

A plurality of nasal aspirators of the bulb suction type is present at the marked. A commonly used nasal aspirator is a bulb and stem made in one piece e.g. by rotation molding. The only opening in the device is at the end of the stem and does not allow proper emptying of the device and makes it impossible to clean the device so that it is free of organic material. Accordingly, this kind of nasal aspirators is not acceptable for repeated use as cross contamination between patients may not be prevented. A nasal aspirator of this kind is known e.g. from US 2007/0270736.

It is also known to provide an opening device on a bulb of the kind described above, to allow emptying the content and to allow flushing of the inner parts of the device. The fastening of a closing device to accommodate a cap into the bulb does, however, result in inner structures inside the device that makes it difficult to clean and that makes it impossible assure that there are now remains of biological material in the bulb after cleaning. Accordingly, it is not accepted for multiple use.

U.S. Pat. No. 2,890,699 describes a nasal suction device of the bulb suction type having a reservoir for the collected material between the bulb and the stem. This idea is further developed in EP0451062. By introducing a reservoir between the bulb and the stem, ingress of mucus into the bulb may be omitted. Accordingly, the bulb part of the devices may be used repeatedly. The devices are, however, relatively complex and requires replacement, or a cleaning procedure, for the reservoir and the stem part.

There is, however, still a need for a simple and easy to use suction device for the upper airways that is simple in use, is intended for multiple use and thus suitable for proper cleaning and inspection. Additionally, it must be possible to sterilize the device by means of simple and effective means such as by means of sterilizing solutions, boiling or autoclaving.

DISCLOSURE OF INVENTION

The above identified task is solved by means of an improved nasal aspirator of the bulb suction type according to claim 1.

The independent claims relates to preferred embodiments of the present nasal aspirator.

DETAILED DESCRIPTION THE INVENTION

Figures 1, 2:
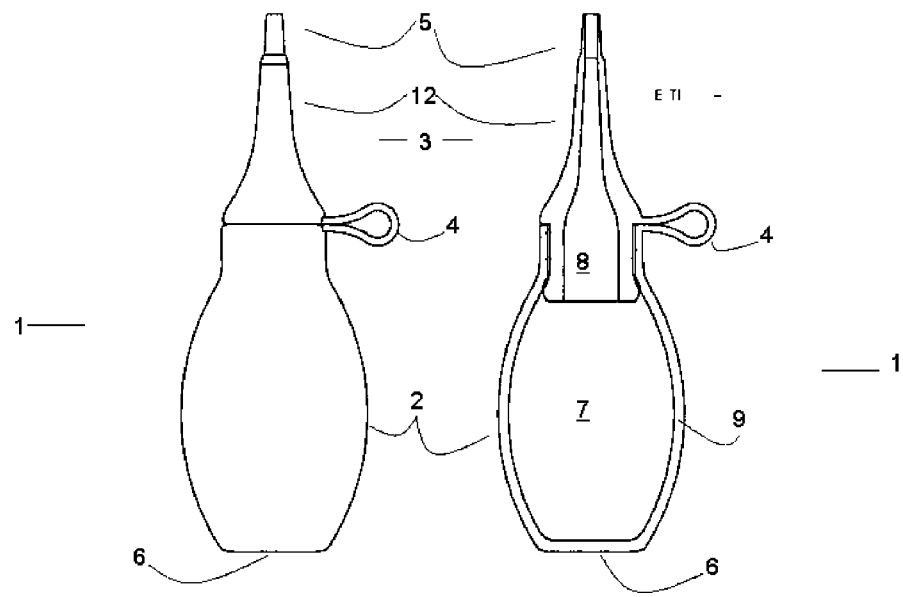
FIG. 1 is a side view of a bulb suction device according to the present invention.
FIG. 2 is a length section along a length axis of the device according to FIG. 1.
Figures 3, 4:
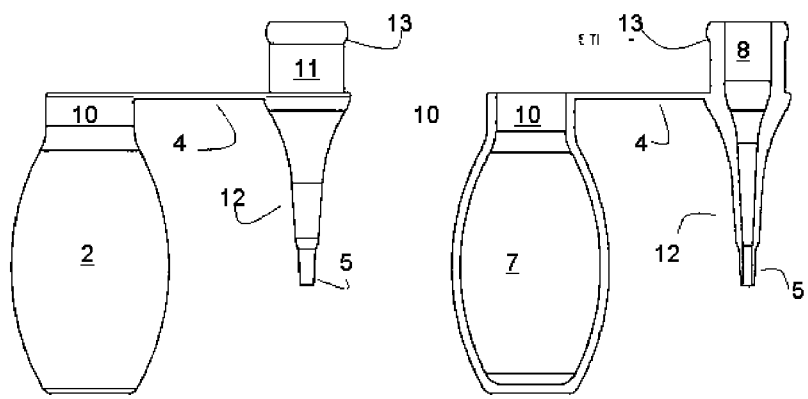
FIG. 3 is a side view of an opened bulb section device as illustrated in FIG. 1.
FIG. 4 is a length section along a length axis of the device according to FIG. 3.
Figures 5, 6:
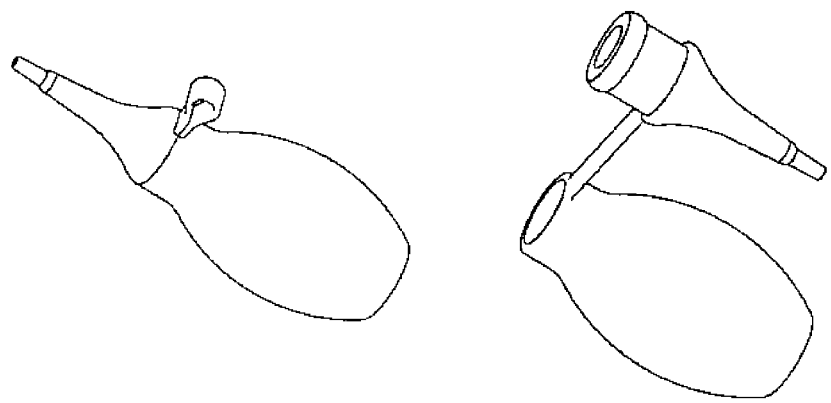
FIG. 5 is a perspective view of the device of FIG. 1.
FIG. 6 is a perspective view of FIG. 3.

The figures illustrate a preferred embodiment of a nasal aspirator 1 according to the present invention. The nasal aspirator 1 comprises a bulb part 2 and a stem part 3, preferably connected by a hinge part 4.

The bulb part 2 comprises a bulb compartment 7 surrounded by a wall 9 made of an elastic material as will be described in more detail below. A flattened portion 6 may be provided as a part of the bulb, to allow the nasal aspirator to stand upright. The flattened portion 6 may be formed as a suction cup to be able to stabilize the device better or to fasten the device to a smooth surface.

The bulb part 2 is provided with a cylindrical neck portion 10 designed to interact with a cap part 11 of the stem part 3.

The inside of the bulb is smooth without any projections or depressions that make it difficult or impossible effectively to clean the inside. The transition between the inside of the bulb and the inside of the neck part thereof is also smooth without edges where organic material may hide during cleaning of the device.

The stem part 3 comprises a cap part 11 and a pipette part 12 having a cylindrical outer surface adapted to fit into the neck portion 10 of the bulb and to give a substantially air tight connection there between. An outwards extending bead designed to interact with the inside of the neck portion to improve the air tightness between the cap and the neck and to avoid that the stem part is unintentionally removed from the bulb part.

A channel 8 is provided through the stem part to give fluid contact between the outer tip 5 thereof and the inner compartment 7 of the bulb. An opening is provided at the outwardly extending part of the outer tip 5. To avoid damage to the nasal mucus due to the sucking force of the device, a radially extending hole may be provided in the outer tip 5.

The present device is preferably connected as illustrated above, so that the bulb part and the stem part are connected by the hinge part to avoid loosing one of the parts when the device is disassembled for cleaning.

The skilled man will understand that the present device also may comprise a cap (not shown) for the stem, or the outer part 5 of the stem to avoid contamination of the device when not in use. The cap may be made of any convenient material. It is also possible to produce a cap of the same material as the suction device in one moulding operation where the parts are moulded in one moulding operation and that the cap is connected to the stem or bulb by a hinge member corresponding to the hinge member connecting the bulb and the stem.

The present device is produced in one or more resilient material(s). According to one embodiment, the device is made in one material that is produced by one single moulding operation, i.e. so that the bulb part, stem part and the hinge part are formed in a single piece in one operation. It is, however, possible to produce the different parts as two or three separate parts that are joined by any available method, such as gluing, welding and press fit mounting.

Preferably, the present device is produced by injection moulding, but other moulding processes, such as rotation moulding, may also be applicable. The skilled man in the art will also understand that the mentioned production methods also allows for choosing different materials for the different parts, or to introduce a different material into one of the parts for adjusting the properties of the finished product.

The present nasal aspirator is made of any suitable polymeric material. Important features of the material(s) is (are):

Resilience, to give the bulb the required elastic properties to be able to produce the required vacuum, and softness of the tip of the stem part to avoid damaging the mucus within the nose.

Mouldability, facilitating a simple and inexpensive production thereof.

Weather resistance, i.e. resistance to degradation and loss of chemical and mechanical properties Resistance to washing and sterilizing liquids, Resistance to sterilization by heat treatment such as boiling and/or autoclaving.

Additionally, it is preferred that the material is transparent to allow easy inspection the inside of the device to control the cleaning thereof.

Presently preferred materials are two component liquid silicones, preferably of a grade accepted for medical use. The skilled man in the art will, however, understand that other polymeric materials that fulfil the requirements indicated above may also be used without departing from scope of the present invention.

The terms "nasal aspirator" and "upper airway aspirator" are used interchangeable in the present description and claims and are both used for suction devices to clear the upper airways such as the nostrils and the mouth.

The invention claimed is:

1. A nasal aspirator comprising:
a resilient bulb;
a stem for suction of liquids by vacuum created by compressing the resilient bulb and thereafter gradually releasing the compression of the resilient bulb where the stem is removably connected to a bulb part;
wherein the bulb part comprises a neck portion adapted to interact with a cap portion of a stem part to create a substantially airtight connection there between;
wherein an inside of the resilient bulb is smooth and without projections or depressions;
wherein the bulb part and the stem part are connected by a hinge member;
wherein the stem portion has ribs in order to engage the neck portion and secure a connection; and
wherein a transition between the inside of the resilient bulb and an inside of the neck portion is smooth and without edges.

2. The nasal aspirator according to claim 1, wherein the cap portion of the stem part is adapted to be inserted into the neck portion of the bulb part.

3. The nasal aspirator claim 1, wherein the nasal aspirator is made of a resilient polymer.

* * * * *